United States Patent [19]

Hubner

[11] Patent Number: 4,642,296
[45] Date of Patent: Feb. 10, 1987

[54] METHOD OF MEASURING THE MAGNITUDE OF AN ENVIRONMENTAL PARAMETER, ESPECIALLY THE CONCENTRATION OF AN EXPLOSION-GENERATING GAS IN A SUBTERRANEAN ATMOSPHERE

[76] Inventor: Hans J. Hubner, Katthagen 24, 4400 Münster, Fed. Rep. of Germany

[21] Appl. No.: 635,329

[22] Filed: Jul. 27, 1984

[30] Foreign Application Priority Data

Jul. 28, 1983 [DE] Fed. Rep. of Germany ....... 3327154

[51] Int. Cl.$^4$ ............................................ G01N 33/00
[52] U.S. Cl. ...................................... 436/138; 73/23; 436/141
[58] Field of Search .................... 73/23, 1 G; 340/632, 340/633, 634; 364/571, 582, 580, 497, 498; 436/141, 143, 136, 137, 152, 138

[56] References Cited

U.S. PATENT DOCUMENTS

| | | | |
|---|---|---|---|
| 3,678,489 | 7/1972 | Scherban et al. | |
| 3,762,878 | 10/1973 | Villalobos | 436/143 |
| 3,790,348 | 2/1974 | Bossart et al. | 436/143 |
| 3,960,495 | 6/1976 | Tantram | 436/141 |
| 4,150,561 | 4/1979 | Zupanick | 73/23 |
| 4,170,892 | 10/1979 | Bailitis | 73/23 |
| 4,272,249 | 6/1981 | D'Antonio | 436/136 |
| 4,372,155 | 2/1983 | Butler et al. | 73/23 |
| 4,457,161 | 7/1984 | Iwanga et al. | 73/23 |

FOREIGN PATENT DOCUMENTS

| | | |
|---|---|---|
| 1908216 | 9/1969 | Fed. Rep. of Germany . |
| 2641165 | 4/1977 | Fed. Rep. of Germany . |
| 2318280 | 11/1977 | Fed. Rep. of Germany . |
| 3027051 | 7/1980 | Fed. Rep. of Germany . |
| 3138046 | 9/1981 | Fed. Rep. of Germany . |
| 3031555 | 3/1982 | Fed. Rep. of Germany . |
| 3142468 | 6/1982 | Fed. Rep. of Germany . |
| 3243542 | 11/1982 | Fed. Rep. of Germany . |
| 1564981 | 1/1977 | United Kingdom . |
| 1462480 | 1/1977 | United Kingdom . |
| 2089993 | 6/1982 | United Kingdom . |

OTHER PUBLICATIONS

"Ein Frei Programmierbares Mikroprozessorgesteuertes Datensystem ...", by D. Voight, published in Messen+Prüfen/automatik—Jul./Aug. 1982.

"Grundlösungen von Aufgaben zur Weiterverarbeitung ...", by G. Strohrmann, Marl, published in Regelungstechnische Praxis 24.Jahrgang 1982, HEFT 8.

"Die Zuverlässigkeit von Messsystemen", by Dr. P. Profos, published in Handbuch der Industriellen Messtechnik (Vulkan-Verlag, Dr. W. Classen, Nachf. GmbH & Co., KG. Essen, 1978).

"Sicher vor allen Gasgefahren durch Vabotector-Ex", Gas Messung, (Gesellschaft für GerätebaumbH & Co.KG), (6/82 3000 B+M).

Article, "Bessere Früherkennung von Grubenrändern mit Kleinrechnern", Authors: Eicker et al.—Glückhauf, 23 Jan. 1975—pp. 59-63.

Page from publication listing Abstracts of Soviet Patents, vol. Y, No. 36, Section for Measuring, Testing—p. 9, 3/1977.

Article, "Ein Frei Progammierbares Mikroprozessorgesteuertes Datensystem ...", Author: Voight, "Messen+Prüfen/Automatik", Jul./Aug. 1982, pp. 475-481.

Article, "HP-IL Data-Acquisition, Control System Opens New Measurement Territory", Author: Scott Scampi; Electronics, Oct. 1982—pp. 105-108.

Article, "Prinzip der Digitalen Linearisierung mit Mikroprozessoren", Author: Dr. Hans Fürst, Elektronic 1978, vol. 7, pp. 81-87.

Primary Examiner—Kenneth M. Schor
Assistant Examiner—K. M. Hastings

[57] ABSTRACT

Explosive gas concentrations in a subterranean atmosphere can be monitored, not by measuring the concentration of the explosive gas directly but, according to the invention, by monitoring a second parameter of the atmosphere, e.g. oxygen concentration, and calculating the level of the combustible gas from this measured value.

3 Claims, 3 Drawing Figures

METHOD OF MEASURING THE MAGNITUDE OF AN ENVIRONMENTAL PARAMETER, ESPECIALLY THE CONCENTRATION OF AN EXPLOSION-GENERATING GAS IN A SUBTERRANEAN ATMOSPHERE

CROSS REFERENCE TO RELATED APPLICATION

This application is related to my copending application Ser. No. 493,696 filed May 11, 1983, now U.S. Pat. No. 4,526,028, based upon German application No. P 32 17 798.4 filed May 12, 1982 and entitled "Process and Device for Indicating and Evaluating Environmental Parameters," U.S. Ser. No. 493,696 being hereby incorporated by reference in its entirety in the present application. See also my concurrently filed copending application Ser. No. 635,324 filed July 27, 1984, now U.S. Pat. No. 4,562,723 and Ser. No. 635,323 filed July 27, 1984, now U.S. Pat. No. 4,569,223.

FIELD OF THE INVENTION

My present invention relates to a method of and to an apparatus or device for determining the magnitude of an environmental parameter, especially the concentration of an atomspheric component, and more particularly, to a method of determining the magnitude of the concentration of a component of a ventilating gas stream, e.g. methane or fire damp in a subterranean ventilating air current for mining applications and the like.

BACKGROUND OF THE INVENTION

It is known, as the aforedescribed applications indicate, to automatically monitor an environmental condition, such as the concentration of methane in a ventilating air current for a mine by analyzing the air for the particular component of concern and comparing the measured values with a normal or desired state to establish an alert condition when and if the level of the component exceeds the predetermined maximum.

In general, moreover, it is known to measure magnitudes of the concentrations of the components of the atmosphere for a variety of applications to obtain long term information regarding the atmosphere or for short term purposes, e.g. to determine whether levels of the various components exceed or fall below desired magnitudes. These measurements are generally done directly utilizing various processes and techniques which have been found to be effective for the different components.

Probably the most significant of these measuring stations are those which are located in environments with potential danger to operating personnel, i.e. to signal the reliability of ventilation, to indicate a condition of potential danger requiring evacuation of personnel or to trigger remedial measurements (e.g. increased ventilation) to eliminate dangerous conditions. Such stations are located in mines and other subterranean facilities.

For the evaluation of the concentrations of the several components, as noted, a variety of measuring systems have been and are used in practice. For example, it is known to measure the concentration of explosive and combustible gases, especially fire damp, hydrogen and most specifically methane, by a system which utilizes a catalytic combustion of the component. This system will be referred to as the "catalytic combustion" system hereinafter. For the measurement of the concentrations of toxic gases, it is known to determine the rate at which such toxic components are chemisorbed on metal oxide semiconductors, this system being referred to hereinafter as the "Chemisorption on Metal Oxide Semiconductor" system. The measurement of the concentration of oxygen can be effected by a process in which the oxygen traverses a membrane and a cathode juxtaposed with an anode across a basic electrolyte, an electric current being thus generated to represent an oxygen concentration. The latter system will be described as the "Chemical Current-Generating System". For the quantitave determination of carbon dioxide, it is common to utilize a measurement in the change of thermal conductivity and hence this system can be referred to as the "Thermal Conductivity" system.

Reference may be made to the "VABOTECTOR-EX" instrument marketed by Firma Gesellschaft fur Geratebau mbH & Co. KG, of the Federal Republic of Germany as described in a brochure 6/82 thereof. Naturally, other parameters of the atmosphere can be measured, these including pressure, temperature, relative humidity and the like by appropriate measuring systems (see the aforementioned applications).

Indeed, even for the measurement of one parameter, it is possible that a number of measuring systems will be required for various reasons and to suit various boundary conditions. This is particularly the case for the measurement of methane concentration of a gas. For high precision at low concentrations, for example, it is known to utilize the catalytic combustion system while for higher concentrations, it may be necessary to utilize the thermal conductivity system. In other words, under certain circumstances where one system may not be available or cannot effectively be used, it may be essential to utilize a second system. A case in point is where the instrument is a battery-powered portable instrument and one system may require a higher energy consumption than another and low battery power may make the use of the high-consumption system ineffective.

As described in my commonly owned German patent application No. P 32 43 542.8-52 (German patent document No. DE-OS 32 43 542), which was published May 30, 1984, a catalytic combustion system is utilized and in the event of a problem, the system can switch over to the thermal conductivity system for measuring methane concentration. The system is utilized to determine approach to a lower explosion limit.

While this system has been found to be highly effective, there is a general problem in this field and that is a problem of sensitive or dangerous instruments or measuring techniques at least for some parameters such as the concentrations of certain components of the gas stream. It is the case with methane for example, and in the case of methane or wherever a sensitive measuring system which is not completely reliable has been used in the past, it is desirable to find a less sensitive or dangerous system for measuring the concentration of the particular component.

OBJECTS OF THE INVENTION

It is the principal object of the present invention to improve upon a system of the type last described and hence to provide a more reliable method of detecting the concentration of methane in a ventilating air current for a mine or the like.

Another object of the invention, in more general terms, is to provide a method of determining the magnitude of a parameter of interest which is not sensitive to the idiosyncrosies or drawbacks of existing measuring systems for that magnitude.

Still another object of the invention is to provide a method of evaluating an environmental parameter which is free from the drawbacks of earlier techniques.

It is also an object of this invention to provide an apparatus or device which can utilize the principles of this invention.

SUMMARY OF THE INVENTION

These objects and others which will become apparent hereinafter are attained, in accordance with the invention, in a method for measuring the magnitude of a first environmental parameter, and especially the concentration of a component in an atmosphere such as a mine atmosphere where that component may be a combustible or explosion-inducing component, which comprises analyzing a second parameter of the atmosphere and measuring the magnitude of this second parameter which is mathematically correlated to the first parameter according to predetermined stored relationships, comparing the measurement of the second parameter thus obtained with the stored relationships and deriving from the stored relationship a corresponding value of the first parameter and, if desired, displaying that parameter.

In other words, instead of measuring the first parameter directly, by a measuring system which is designed for such measurement, a second measuring system is used to measure the second parameter which is correlated to the first and the magnitude of the first parameter is calculated from the aforementioned correlation.

The invention is based upon the fact that the various parameters of the atmosphere are so correlated that variation of one parameter will result in a corresponding variation of a dependent parameter in a completely reliable and mathematically determinable way. Consequently, I substitute a measurement of the second parameter for the measurement of the first and can carry out the measurement with greater ease, accuracy and reliability upon this second parameter than existing technology allows me to use if I were to determine the first parameter directly.

Naturally, the invention can be utilized in three distinct process principles.

In the first, I may measure a parameter which corresponds to the parameter I wish to determine, i.e. a parameter with the same relationship, e.g. concentration. In that case, I substitute a measurement of one concentration for the desired value of another concentration.

In a second operating principle, I may measure a parameter with a different reference or relationship as a substitute for the parameter of interest. For example, I may measure the partial pressure of a gas component in order to determine the concentration of another gas component.

In the third operating mode, I may substitute a magnitude with a determined reference by another parameter with a different reference.

The only requirement, of course, is that whatever the parameter which is actually measured, it must have a well-defined reproducible mathematical relationship to the parameter of interest which can be displayed, recorded or utilized for control purposes. All three are referred to herein as the step of operating upon this parameter.

The invention is applicable to the measurement of the concentration of explosion-inducing gases, e.g. fire damp or methane. When the concentration of an explosive gas is to be measured, at least in circumstances in which the catalytic combustion system is not advantageous or may be out of service, the concentration of the explosive gas can be measured according to the invention by simply measuring the concentration of another gas component whose concentration depends upon that of the explosive gas in the mine atmosphere. The "substitution" which is effected by the invention is not, of course, an actual replacement of the explosive gas in the atmosphere by another gas, but rather is a replacement of the measurement procedure which would be utilized for the explosive gas by a measurement procedure which responds to the correlated gas component in combination with a mathematic determination of the explosive gas concentration from the magnitude of the other component which is actually measured.

It is important that the concentration of the replacement-measurement gas component, therefore, be precisely correlated to the methane concentration.

In a mining atmosphere this has been found to be the case where the measured gas is oxygen.

Air is practically stable in composition with 78% nitrogen and 21% oxygen. When a concentration of 5% methane develops in the air, the oxygen concentration will be reduced to 19.95%, the ratio of the concentrations of oxygen and nitrogen remaining the same in spite of the addition of other gases.

Consequently, as the methane concentration in the mine atmosphere increases, there is a reduction in the concentration of oxygen and a corresponding reduction in the concentration of nitrogen.

If one can be certain that as the additional gas only the methane is added, the reduction in the concentration of oxygen can be qualitatively and quantitatively ascribed to the increase in the concentration of methane and by measuring utilizing the chemical current generating system, the oxygen concentration and appropriate calculations, a highly exact determination of the parameter of interest, namely, the methane concentration, can be obtained.

Naturally, in mine atmospheres other inputs can be provided with calculation, and the normal environmental parameters and other gas concentrations can be taken into consideration to ensure the accuracy of the correlation between the methane concentration and the measured oxygen concentration.

Consequently, I prefer to use the measurement of the oxygen concentration to determine methane concentrations well above the lower explosion limit where, for safety reasons or otherwise, the thermal conductivity measuring system may not be desirable.

Furthermore, the present system allows me to replace the thermal conductivity system utilized in the system described in the German patent document No. DE-OS 32 43 542 by the chemical current generating system for oxygen determination, associated with the appropriate calculation. It will be understood that this application also covers such a substitute in the system of the last-mentioned German application.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
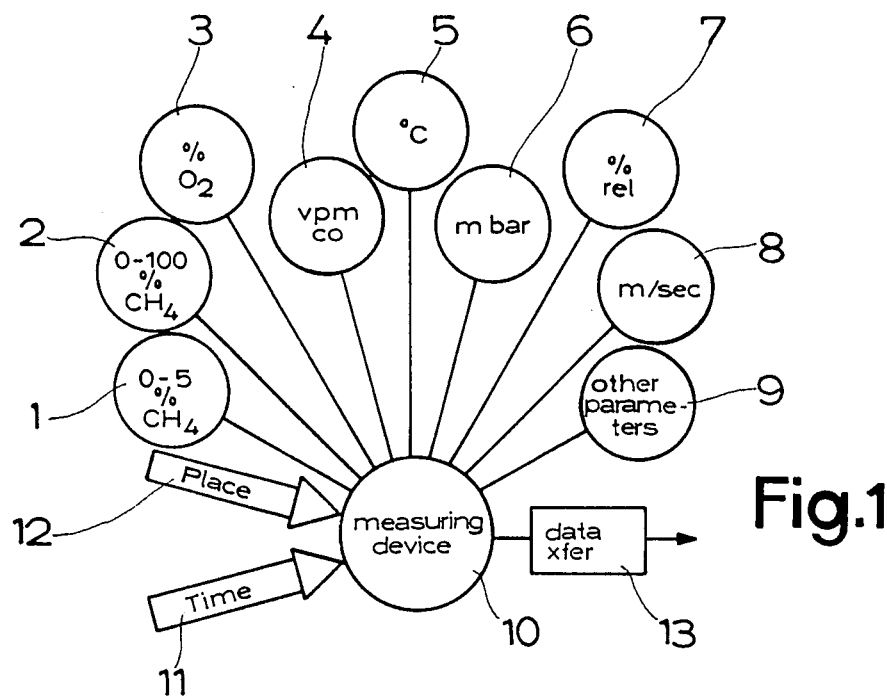
FIG. 1 is a diagram of the functional relationship of the measurement and evaluation of parameters of an atmosphere, especially the ventilating stream of a mine gallery or other subterranean structure.
Figure 2:
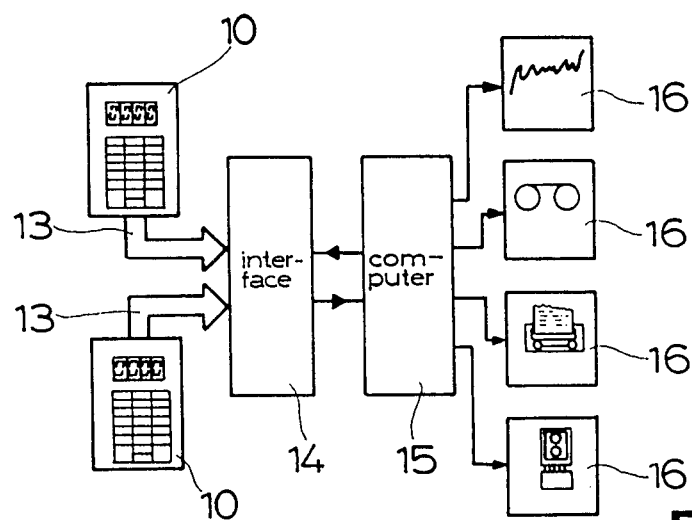
FIG. 2 is a block diagram of an apparatus for measuring and evaluating the parameters of such an atmosphere.

For a more detailed explanation of FIGS. 1 and 2 of the drawing, reference may be had to the above-mentioned copending application.

In the diagram of FIG. 1, reference numerals 1–4 identify different gas-concentration inputs to the measuring system represented at 10, while reference numerals 5–8 represent nonconcentration parameters, namely the air temperature, the air pressure, the relative humidity and the air velocity. Other parameters may also be fed to the measuring device 10 as represented at 9, 11 and 12 represent data inputs signalling the time and place of the measurement and the device 10 may input data as represented at 13 to a central processing unit by any remote transmission means. The device 10 can be a portable unit moved from place to place in the mine.

The inputs to the measuring device 10 include a first methane concentration input 1 which can measure methane concentrations up to 5% methane, e.g. a catalytic combustion system, a second methane concentration input 2 evaluating methane with lesser accuracy to concentrations up to 100% and operating by the thermal conductivity method, an oxygen concentration measuring system effective in the concentration range of 0 to 21% utilizing the chemical current generating system, and a carbon monoxide concentration measuring system effective for values up to 300 vpm and utilizing the chemisorption on metal oxide-semiconductor system. For safety reasons, when the methane concentration exceeds 5%, the second measuring system 2 is brought into play, and in the event this system should fail or in place of this system, the oxygen measuring system can be used.

Figure 3:
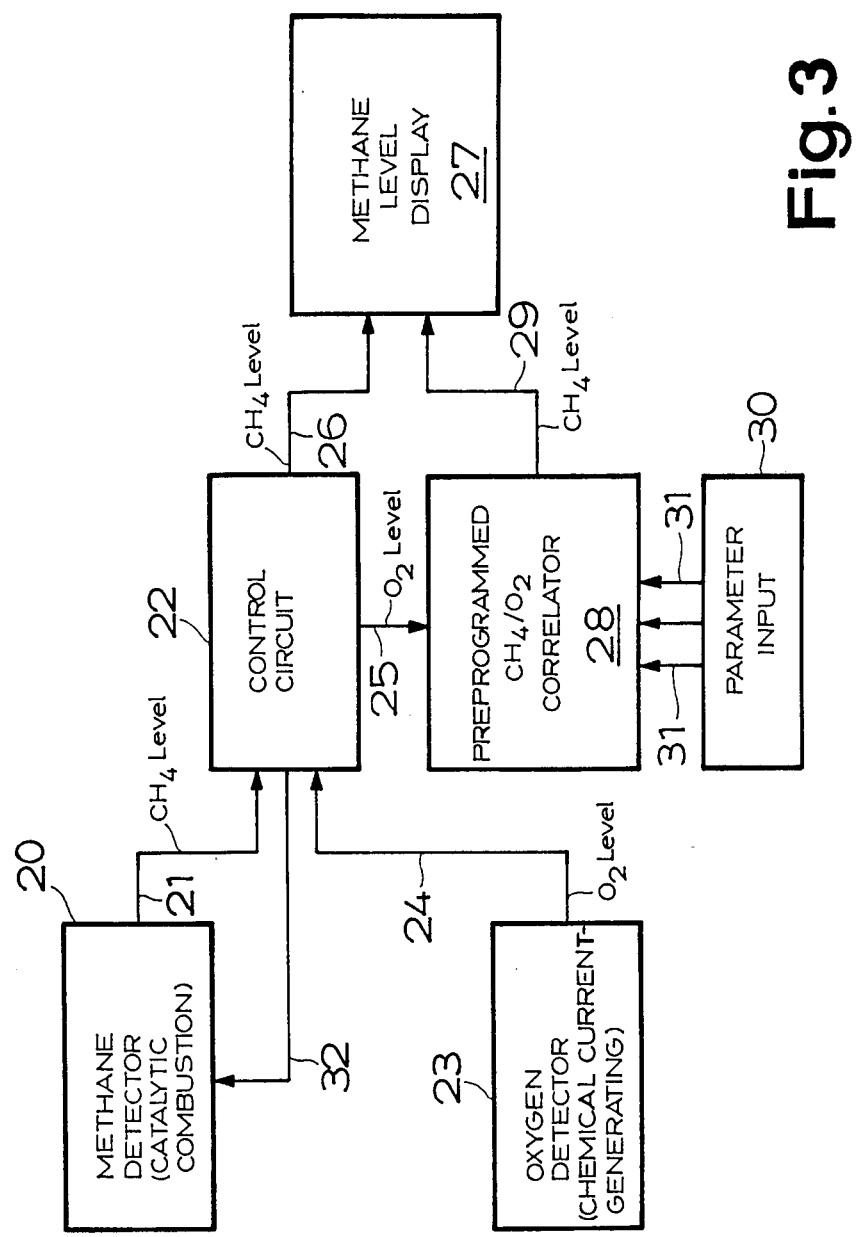
FIG. 3 is another block diagram illustrating the principles of this invention.

Referring to FIG. 3, it should be noted that when one is certain that only the methane is added to the atmosphere, the oxygen detector 3 can be used. In particular, the system can comprise the catalytic combustion methane detector 20 feeding a methane level input at 21 to a control circuit 22 which transfers the methane level signal at 26 to a display or other processing unit 27. When the control circuit finds that the methane level is approaching the lower explosive limit, the methane detector 20 is cut out by the signal 32 and the output from the chemical current generating oxygen detector 23 is fed via the oxygen level data line 24 to the control circuit 22. The oxygen level is applied at 25 to a computer whose memory has been preprogrammed with the methane/oxygen correlation, this unit being referred to as a preprogrammed correlator at 28 which delivers the calculated methane level via data line 29 to the display 27. Since other parameters may be required for the calculation, they may be supplied as represented by the parameter input 30 as data 31.

FIG. 2 shows an apparatus for measuring and evaluating the parameters of the atmosphere which comprises two measuring units 10 representative of a multiplicity of such units which have not been illustrated except for these two. These units are connected to a control and signal transfer network 14 which can be coupled to a central computer 15 with which various peripheral and terminal units 16 can be connected as described in the aforementioned copending U.S. application.

The computer 15 and the peripheral ports and terminals represent the control circuit 22, the correlator 28 and the display 27 previously described. When the oxygen detector 23 is used to supply the methane level as described, the thermal conductivity measuring system 2 can be cut out. Especially precise results are obtained when the methane concentration is calculated from the oxygen concentration in the central computer 15.

I claim:

1. A method of determining the concentration of methane in a mine-ventilation current or other closed-system atmosphere, the atmopshere comprising, apart from methane and some elements in negligible concentrations, only nitrogen and oxygen, a correlation between the concentration of methane added to said atmosphere and the concentration of oxygen in said atmosphere being known from a law equating oxygen concentration with addition of methane to atmospheric air, which comprises the steps of:

at concentrations of methane of up to a threshold value of about 5% of methane measuring the concentration of methane in said atmosphere directly; and at concentrations of methane above said threshold value, discontinuing the direct measurement of the concentration of methane, measuring the concentration of oxygen in said atmosphere, mathematically determining from said correlation the concentration of methane as correlated to the measured concentration of oxygen, and using the mathematically determined value of the concentration of methane instead of the directly measured value.

2. The method defined in claim 1 wherein the concentration of methane in said atmosphere is measured by catalytic combustion.

3. The method defined in claim 1 wherein the concentration of oxygen is measured by chemical current generation.

* * * * *